United States Patent [19]
Takeuchi et al.

[11] 4,386,054
[45] May 31, 1983

[54] SPIN IMMUNOASSAY APPARATUS

[75] Inventors: Makoto Takeuchi; Ekuo Yoshida; Masahiro Kohno, all of Akishimashi, Japan

[73] Assignee: JEOL Ltd., Tokyo, Japan

[21] Appl. No.: 310,745

[22] Filed: Oct. 13, 1981

[51] Int. Cl.³ ........................................... G01N 33/16
[52] U.S. Cl. ...................... 422/63; 422/64; 436/173; 436/808
[58] Field of Search .................. 422/63, 64; 424/12; 23/230 B

[56] References Cited
U.S. PATENT DOCUMENTS

| | | | |
|---|---|---|---|
| 3,887,698 | 6/1975 | McConnell et al. | 424/12 |
| 4,155,978 | 5/1979 | Naono et al. | 422/64 |
| 4,224,032 | 9/1980 | Glover et al. | 422/64 X |

*Primary Examiner*—Robert L. Lindsay, Jr.
*Attorney, Agent, or Firm*—Webb, Burden, Robinson & Webb

[57] ABSTRACT

A spin immunoassay apparatus includes means for sampling one of a plurality of sample solutions, a system for measuring certain amounts of the sample solution, a reaction system for mixing the sample solution with reagent which consists of antibody coupled with spin labelled antigen by antigen-antibody reaction and incubating the mixture for a certain period of time, and an electron spin resonance device for measuring the concentration of a spin labelled material extricated. The electron spin resonance device has a cavity resonator including a fixed cell. A flow system transfers the mixed sample solution and reagent into the cell. The intensity of a magnetic field applied to the cell is adjusted so that the maximum differential value or the minimum differential value of the ESR signal of the spin labelled material will be detected.

3 Claims, 2 Drawing Figures

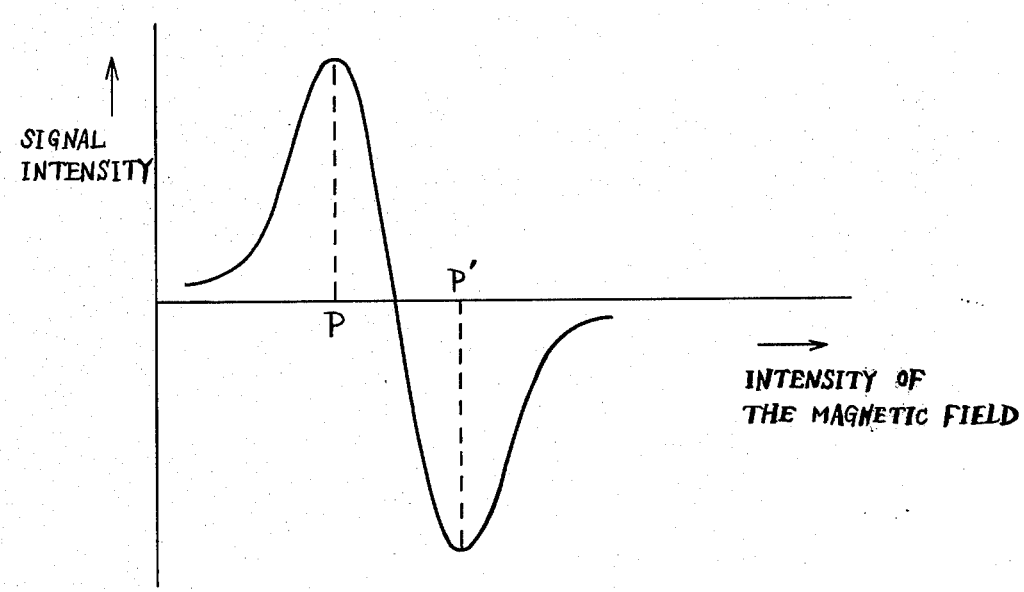

SPIN IMMUNOASSAY APPARATUS

BACKGROUND OF THE INVENTION

1. Field of the Invention

The present invention relates to a spin immunoassay apparatus for monitoring the concentration of drug used for therapeutic purpose in physiological fluids.

2. Prior Art

There have heretofore been used immunoassay apparatus (known as radioimmunoassay apparatus) for enabling the operator to observe antigen-antibody reactions with a radioisotope used as the labelling agent in monitoring the concentration in physiological fluids and the amount of excretion of a variety of drugs used for therapeutic purpose. Since the prior apparatus relies on the radioisotope, the operator and other persons involved in the handling of the apparatus are likely to be exposed to radiation, and the apparatus requires expensive facilities to dispose of the used radioisotope which would otherwise cause environmental contamination if left abandoned. The radioisotope is unstable as it has a certain half-life. The known apparatus are also disadvantageous in that they take a lengthy period of time, a few hours to twenty-four hours, for measurement which involves a preparation stage up to a post treatment stage, and hence are unsuitable for use with emergency tests.

The foregoing difficulties could be avoided by using a spin immunoassay apparatus which relies on stable free radicals as a labelling agent in enabling the operator to observe antigen-antibody reaction. More specifically, a sample (human urine, for example) is put into a test tube and a reagent made of a spin labelled antigen is added to the sample. The mixture is sufficiently blended, incubated for a certain interval of time in a bath of water at a temperature of 37° C., and transferred into a sample cell. The sample cell is inserted into a cavity resonator of an electron spin resonance (ESR) device so as to produce an ESR spectrum of the spin labelling agent. The difference (peak-to-peak value) between maximum and minimum differential values of the spectrum can be regarded as the concentration of free lavelled antigen released from antibody. With this process, however, sample cells tend to be located at varying positions in the cavity resonator causing fluctuation of the quality factor of the cavity resonator. Therefore, the peak-to-peak values greatly vary according to the position of the cell in the cavity resonator.

A process proposed to eliminate the above problems would be to place a calibration sample (for instance, a substance containing $Mn^{2+}$) in the cavity resonator which remains left in the cavity resonator, measure the ESR spectrum of the calibration sample and a sample to be tested at the same time, and calibrate the ESR spectrum of the sample tested with the ESR spectrum of the calibration sample. The proposed process however suffers from the following defects: first, although a peak-to-peak value of the sample being tested can be obtained by sweeping the intensity of the magnetic field within just the range of resonant signal, a resonant signal for calibration from the calibration sample should be measured at the same time, resulting in an increased area to be swept and a prolonged period of time required for measurement; secondly, when a signal which is much less (for example, 1/100) intensive than a calibration signal which is automatically calibrated by a data processor, digital noises reduce accuracy of measurement even if the calibration signal is adjusted to have its maximum value scaled by full bits of an analog to digital (A/D) converter, since the number of bits assigned to the signal being tested is 1/100 of the number of the full bits. Where the A/D converter has a resolving power of 10 bits and an accuracy of $\frac{1}{2}$, the least significant bit (LSB), an error of ±5% occurs at this stage; thirdly the proposed process is tedious and time-consuming.

SUMMARY OF THE INVENTION

Briefly a spin immunoassay system is provided comprising an automatic apparatus for sampling and measuring one of a plurality of specimen solutions, automatic apparatus for mixing the specimen solution with reagent which consists of antibody coupled with spin labelled antigen by antigen-antibody reaction, and apparatus for incubating the mixture for a period of time. The immunoassay system further comprises an electron spin resonance device for measuring the concentration of a spin labelled material extricated. The electron spin resonance device has a cavity resonator with a fixed testing cell. A flow system is provided to transfer the incubated specimen and reagent mixture into the testing cell. The intensity of a magnetic field of the ESR applied to the testing cell is adjusted so that the maximum differential value or the minimum differential value of the ESR signal of the spin labelled material will be detected.

Accordingly, it is an object of the present invention to provide a spin immunoassay apparatus which will analyze samples in a much shorter period of time.

Another object of the present invention is to provide a spin immunoassay apparatus which can be handled with ease.

Still another object of the present invention is to provide a spin immunoassay apparatus having an increased accuracy of measurement and an improved signal-to-noise ratio.

BRIEF DESCRIPTION OF THE DRAWINGS

The above and further objects and novel features of the invention will more fully appear from the following detailed description when the same is read in connection with the accompanying drawings. It is to be understood, however, that the drawings are for the purpose of illustration only and are not intended as a definition of the limits of the invention.

FIG. 2 is a graph of a signal waveform produced during operation of the spin immunoassay apparatus of the invention.

DETAILED DESCRIPTION OF THE PREFERRED EMBODIMENT

Figure 1:
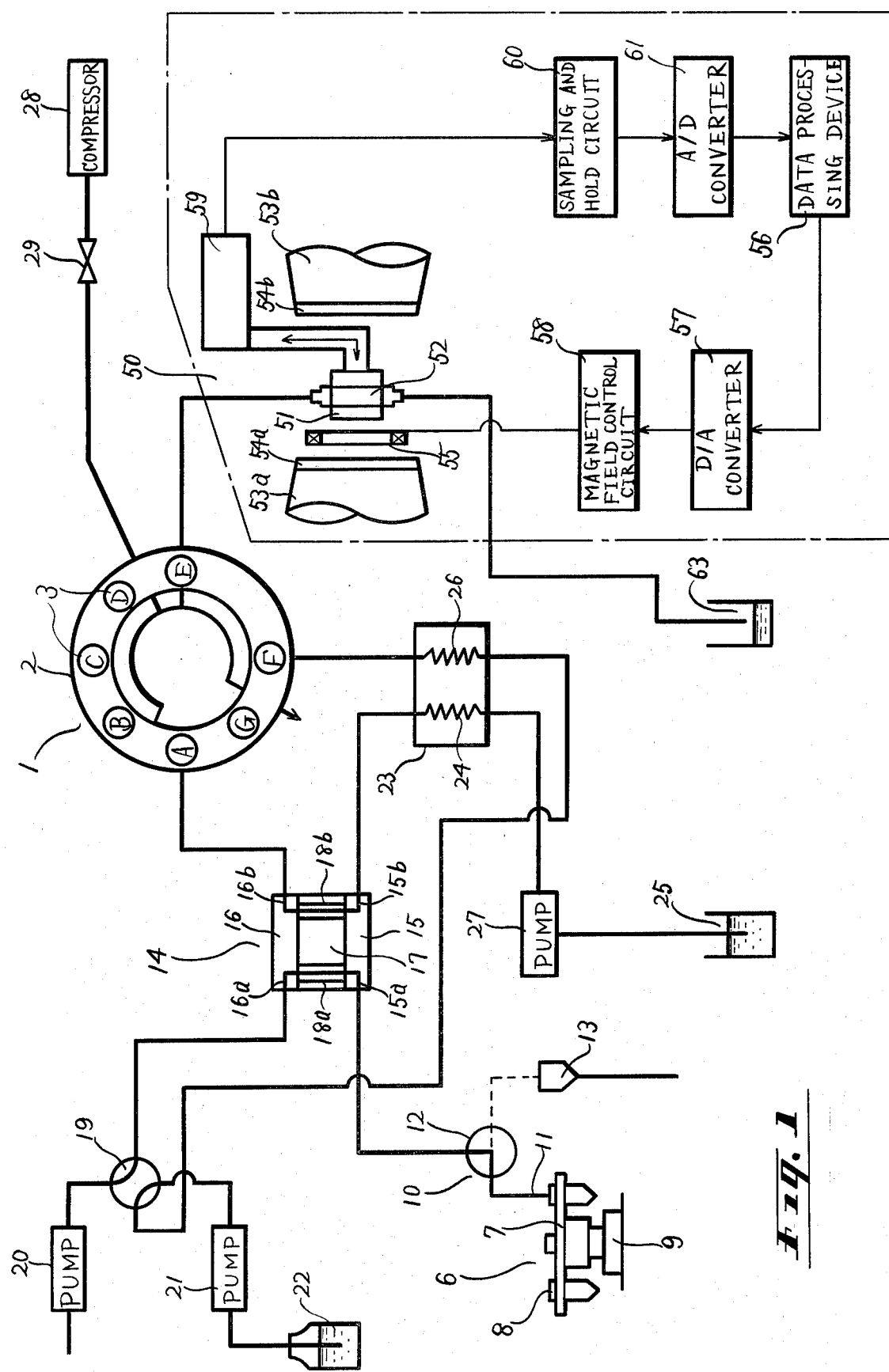
FIG. 1 is a diagrammatic illustration of a spin immunoassay apparatus according to a preferred embodiment of the present invention.

As shown in FIG. 1, a reaction device 1 (see U.S. Pat. No. 4,155,978 for details of this reaction device) comprises a rotatable body 2 and a plurality of reaction tubes 3 supported on the rotatable body 2, the body 2 being intermittently rotatable as by a geneva gear. The reaction tubes 3 are located at positions indicated by A, B, C, D, E, F, and G. Samples and reagents are introduced into the reaction tubes 3 at the position A at all times. While the reaction tubes 3 move from the position A to the position B, a gas is supplied to the reaction tubes 3 from a compressor 28 via a valve 29 to stir the sample and reagent solution therein with bubbles. Upon arrival at the position E, the sample solution is introduced by compressed air or nitrogen gas into a cell 52 in a cavity resonator 51 of an electron spin resonance device 50, where the sample and reagent solution is measured for electron spin resonance. After the measurement has been finished, the sample and reagent solution in the cell 52 is discharged by the compressed air or nitrogen gas into a discharge tank 63.

The reaction tubes 3 are washed at the position F, and the washing liquid is discharged at the position G. A sample dispensing device 6 comprises a turntable 7, a plurality of sample tubes 8 supported on the turntable 7 around its periphery, and a means 9 for driving the turntable 7, each of the sample tubes 8 containing a sample liquid to be measured. A sampling head 10 includes a suction pipe 11 and a device 12 for shifting the suction pipe 11. The suction pipe 11 has a tip or lower end thereof inserted into one of the sample tubes 8 which is in a particular position for drawing up the sample liquid out of the sample tube 8. The suction pipe 11 is movable to a wash tank 13 as indicated by the broken line in which the lower end of the suction pipe 11 can be washed. A sampling valve 14 comprises a pair of spaced fixed members 15, 16 and a rotatable member 17 interposed therebetween and having at least two passages 18a and 18b. The fixed member 15 has a passageway 15a connected to the sampling head 10, and the fixed member 16 has a passageway 16a connected to a changeover valve 19. The changeover valve 19 selectively connects the passageway 16a to either a pump 20 or a pump 21. When the pump 20 is connected by the changeover valve 19 to the passageway 16a as illustrated, the sample solution is sucked out of the sample tube 8 and introduced into the passage 18a in the rotatable member 17. When the changeover valve 19 is changed over to connect the pump 21 to the passageway 16a, the pump 21 sucks a washing liquid from a washing liquid tank 22 and forces the washing liquid to flow through and hence flush out a sample weighing system including the sampling valve 14.

The fixed member 16 also has a passageway 16b connected to the reaction tube at the position A in the reaction device. The fixed member 15 also has a passageway 15b connected through a thru-pipe 24 in a preheating block 23 and pump 27 to a reagent tank 25. Thus, a reagent is fed by the pump 27 from the reagent tank 25 via the pipe 24 into the reaction tube 3 supported on the rotatable body 2 at the position A. A pipe 26 in the preheating block 23 carries the washing liquid pushed by pump 21 into the reaction tube 3 at the position F on the rotatable body 2. The compressor 28 supplies compressed air or nitrogen gas via the valve 29 to the reaction tube at the position midway between the positions A and B for bubble stirring purposes, to the reaction tube at the position E for introducing and discharging the sample solution, and to the reaction tube at position midway between the positions F and G for discharging the washing liquid.

The electron spin resonance device 50 includes a pair of spaced permanent magnets 53a and 53b, respectively. The cavity resonator 51 with the cell 52 and an auxiliary coil 55 are disposed between the magnetic pole pieces 54a and 54b. An electric current is supplied to the auxiliary coil 55 from a data processing device 56 such as a digital electronic computer through a D/A converter 57 and a magnetic field control circuit 58.

A circuit 59 in the electron spin resonance device 50 comprises, although not shown, a high-frequency oscillator for supplying a high frequency signal (for example, 100 kHz) to a modulation coil (not illustrated) disposed between the auxiliary coil 55 and the cavity resonator 51, a microwave oscillator for supplying a microwave of a fixed frequency to the cavity resonator 51 via a magic tee or a circulator, a microwave detector for detecting a microwave reflected from the cavity resonator 51 through the magic tee or the circulator, an amplifier for amplifying the output from the microwave detector, and a synchronous detection circuit for selectively detecting a signal out of the output from the amplifier which is in phase with the high-frequency signal as modulated. The circuit 59 produces an output which is delivered to the data processing device 56 via a gated integration and sampling and hold circuit 60 for integrating an input thereto for a given period of time and holding the integrated value, and an A/D converter 61. The reaction device 1, the sampling valve 14, the preheating block 23, and the cavity resonator 51, cell 52, magnets 53a, 53b, auxiliary coil 55 and others of the electron spin resonance device 50 are disposed in an air bath maintained at a temperature of about 37° C., with the temperature regulation within ±0.05° C.

The apparatus thus constructed will operate as follows: A certain amount of sample (for example, human urine) is supplied from the sample dispensing device 6 into the reaction tube 3 at the position A on the rotatable body 2. A certain amount of reagent is also supplied from the reagent tank 25 into the reaction tube 3 at the position A. While the reaction tube 3 is moving from the position A to the position B, the sample solution and the reagent solution is well stirred with bubbles to mix the sample and the reagent together to form a homogenous solution. At this time, a substitution reaction takes place which can be expressed by the following equation:

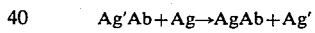

$$Ag'Ab + Ag \rightarrow AgAb + Ag'$$

where Ag' is the spin labelled antigen, Ag'Ab is a reagent which consists of an antibody coupled with the spin labelled antigen by antigen-antibody reaction, and Ag is a substance to be detected in the sample such as a medicinal substance.

While the mixture solution is moving from the position B to the position E during a certain period of time (about several to ten minutes, for example), the mixture solution is incubated in the air bath kept at a fixed temperature (about 37° C.), and a spin labelled material in the reagent and a medicinal substance in the sample are exchanged with each other, extricating the spin labelled material. When the process of exchange is in equilibrium, the solution to be tested in the reaction tube 3 at the position E is introduced under the pressure of compressed air or nitrogen gas into the cell 52 in the cavity resonator 51 of the electron spin resonance device 50. The unreacted reagent in the cell 52 can produce the spectrum of a resonance signal with line broadening. Such spectrum will become undetected by synchronous detection due to magnetic field modulation at a frequency of 100 kHz. The spin labelled material as extricated from the antibody by replacing the medicinal substance can produce a sharp resonance signal upon synchronous detection. The intensity of this resonance signal is in proportion to the concentration of the extricated spin labelled material, that is, the amount of medicinal substance since the concentration of the spin labelled material is proportional to the amount of medicinal substance. The auxiliary coil 55 is controlled by the data processing device 56 to adjust the intensity of a magnetic field between the magnets 53a and 53b into P or P' gauss so that the maximum differential value or the minimum differential value of the electron spin resonance signal produced from the spin labelled material in the sample solution in the cell 52 will be detected. Thus, the synchronous detection circuit in the circuit 59 can detect a resonance signal which corresponds to a magnetic field of P or P' gauss as shown in FIG. 2. The detected signal is integrated for a given period of time by the gated integration and sampling and hold circuit 60.

In the other embodiment, the maximum differential signal and the minimum differential signal are obtained by switching the magnetic field into P and P' gauss by the auxiliary coil 55 and integrated for a given period of time respectively. The integrated mimimum differential signal is changed in polarity and added with the integrated maximum differential signal so as to offset the drift of the base line of the spin resonance signal.

While in the illustrated embodiment only one reagent tank is shown, a plurality of reagent tanks may be provided dependent on the number of testing items, and a plurality of reagents may selectively be supplied to the reaction device as desired.

With the arrangement of the present invention, no process of sweeping the magnetic field is necessary resulting in a greatly reduced period of time required for measurement and improved handleability of the apparatus. With the cell fixed in the cavity resonator of the electron spin resonance device, a sample and reagent in solution form can be supplied and discharged under the control of a flow system with a resulting increased degree of measurement accuracy. Since electron spin resonance measurement is carried out with a magnetic field set at a fixed point (a point which gives a maximum or minimum differential value), there is provided a measurement system having a wide dynamic range for higher measurement accuracy and a better signal-to-noise ratio than those attained conventionally.

Having thus described the invention with the detail and particularity required by the Patent Laws, what is desired protected by Letters Patent is set forth in the following claims.

We claim:

1. A spin immunoassay system comprising automatic means for sampling one of a plurality of specimen solutions, an automatic reaction system for mixing the sample solution with reagent which consists of antibody coupled with a spin-labelled antigen by antigen-antibody reaction, an electron spin resonance device having a cavity resonator having a fixed testing cell, said electron spin resonance device providing a magnetic field in the vicinity of the fixed testing cell and means for adjusting the intensity of said field such that a maximum or minimum differential value of an electron spin resonance signal of the spin-labelled agent will be detected, and means comprising conduits for transferring the mixed specimen solution and reagent into said fixed cell in the cavity resonator of the electron spin resonance device.

2. A spin immunoassay apparatus according to claim 1, in which said means for adjusting the field intensity is adjusted so that maximum and minimum differential values of an electron spin resonance signal of the spin-labelled agent may be detected, means to detect said differential values and means to integrate said differential values for the same period of time respectively, means to change the polarity of the integrated minimum differential signal and to add it to the integrated maximum differential signal.

3. The system according to claim 1 wherein the means for adjusting comprises a data processing device that inputs a signal indicative of the differential intensity signal and outputs a signal via a digital to analog converter to an auxiliary magnet coil for automatically adjusting the magnetic field in the vicinity of the cell to have an intensity corresponding to a maximum or minimum differential resonance signal.

* * * * *

UNITED STATES PATENT AND TRADEMARK OFFICE
CERTIFICATE OF CORRECTION

PATENT NO. : 4,386,054
DATED : May 31, 1983
INVENTOR(S) : Makoto Takeuchi et al.

It is certified that error appears in the above-identified patent and that said Letters Patent are hereby corrected as shown below:

On the title page add:

[30] Foreign Application Priority Data

Oct. 15, 1980 Japan 55-143889--.

Signed and Sealed this

Eighteenth Day of October 1983

[SEAL]

Attest:

GERALD J. MOSSINGHOFF

Attesting Officer

Commissioner of Patents and Trademarks